United States Patent
Wheeler et al.

(10) Patent No.: US 6,344,359 B1
(45) Date of Patent: Feb. 5, 2002

(54) SPECTROPHOTOMETRIC ASSAY FOR THE DETERMINATION OF TOTAL VANADIUM AND THE +IV AND +V OXIDATION STATES OF VANADIUM

(75) Inventors: Jeffery Wheeler, Vancouver; Zaihui Zhang, Vancover, both of (CA)

(73) Assignee: Kinetek Pharmaceuticals, Inc., Vancouver (CA)

( * ) Notice: Subject to any disclaimer, the term of this patent is extended or adjusted under 35 U.S.C. 154(b) by 0 days.

(21) Appl. No.: 09/360,480

(22) Filed: Jul. 23, 1999

Related U.S. Application Data
(60) Provisional application No. 60/095,729, filed on Aug. 7, 1998.

(51) Int. Cl.⁷ .............................................. G01N 33/20
(52) U.S. Cl. ............................. 436/73; 422/61; 436/74; 436/83; 436/166
(58) Field of Search .............................. 436/73–74, 83, 436/166; 422/61

(56) References Cited

U.S. PATENT DOCUMENTS

| | | |
|---|---|---|
| 4,920,057 A | 4/1990 | Castenada |
| 5,376,552 A | 12/1994 | Tokuda et al. |

OTHER PUBLICATIONS

S. Saccubai et al, Indian J. Chem. 1970, 8, 533–535.*
B. Sundar et al, Egypt. J. Chem. 1985, 28, 375–382.*
R. Varma et al, Chem. Anal. 1997, 42, 71–74.*
B. S. Sekhon et al, J. Electrochem. Soc. India 1998, 47, 129–131.*
R. S. Chauhan et al, Chem. Anal. (Warsaw) 1993, 38, 75–82.*
S. P. Arya et al, J. Indian Chem. Soc. 1997, 74, 66–67.*
R. L. Varma et al, Chem. Anal. (Warsaw) 1997, 42, 71–74.*
A. C. Gonzalez–Baro et al, Montsh. Chem. 1997, 128, 323–335.*
F. Zharovskii et al, Chem. Abstr. 1970, 73, abstract 521 09.*
B. S. Sundar et al, J. Inorg. Nucl. Chem. 1981, 43, 404–405.*
B. S. Sundar et al, Chem. Abstr. 1987, abstract 224038d.*
V. Conte et al, J. Org. Chem. 1988, 53, 1665–1669.*
Ahmed, et al. "Non–extrative Spectrophotometric Determination of Vanadium(v) in Alloys and Environmental, Biological and Soil Samples Using 5,7–Dibromo–8–hydroxyquinoline", Analyst, Jul. 1995, V.120. pp. 2019–2023.
Tsai, et al. "Speciation of Vandium(v) and Vandium(iv) with 4–(2 Pyridylazo) Resorcinol Using High Performance Liquid Chromatography with Spectrophotometric Detection", Analyst, Mar. 1994, V.119, pp. 403–407.
Rao, et al. "Effect of Substitution in the Oxine Molecule on the Formation and Extraction of Vandium(V) Complexes" Acta Ciencia, Indica, 1982, V. 8, pp. 69–77.

Barrera et al. "Comparative Study of Spectrophotometric Determination of Vanadium with 8–Hydroxyquinoline" Acta Quimica Compostelana, 1981, V.8, No. 2, pp. 45–53.
Heitner–Wirguin, et al. "Spectrophotometric Determination of Micro–Amounts of Vanadium with 5,7–Di–Iodo–8–Hydroxyquinoline" Talanta, 1967, V. 14, pp. 671–675.
Syamal, "Spectroscopic Studies of Oxovanadium(IV) Complexes of Biguanide, Dibiguanides and 0–Methyl–1–amidinourea", Indian Journal of Pure and Applied Physics, Feb. 1983, V.21, pp. 130–132.
Keller, et al, "Spectrophotometric and ESR Evidence for Vanadium (IV) Deferoxamine Complexes", J. of Inorganic Biochemistry, 1991, V. 41, pp. 269–276.
Rodriguez, et al "A Simple Spectrophometric Determination of Submicromolar Quantities of Vanadium Oxyions", J. of Pharmaceutical and Biomedical Analysis, V. 12, No. 12, 1994, pp. 1597–1599.
Elvingson, et al. "Speciation in Vanadium Bioinorganic Systems . . . ", Inorg. Chem. 1966, V. 35 pp. 3388–3393.
Mravcova, et al. "Effects of Orally Administered Vanadium on the Immune System and Bone Metabolism in Experimental Animals", The Sci. of the Total Env. Supp. 1993, Elsevier Science Publishers, Amsterdam, pp. 663–669.
Takaya, et al. "Speciation of Vanadium (IV) and Vanadium (V) Using Ion–exchange Chromatography and ICP–AES", Nat. Inst. Of Ind. Health, 1994, V.32, pp. 165–178.
Hanson, et al., "Characterization of the Potent Insulin Mimetic . . . ", Inorg. Chem., 1966, V. 35, pp. 6507–6512.
Sun, et al., "Oxidation Kinetics of the Potent Insulin Mimetic . . . ", Inorg. Chem., 1966, V. 35, pp. 1667–1673.
Baveja, et al., "Spectrophotometric Determination of Vanadium in Complex . . . ", Intern. J. Environ. Anal. Chem., 1984, V. 17, pp. 299–306.
Pardoll, et al., "Exposing the Immunology of Naked DNA Vaccines", Immunity, V. 3, Aug. 1995, pp. 165–169.

* cited by examiner

*Primary Examiner*—Arlen Soderquist
(74) *Attorney, Agent, or Firm*—Bozicevic Field & Francis LLP; Pamela J. Sherwood

(57) ABSTRACT

A rapid colorimetric assay is provided for determining the concentration of vanadyl and vanadate ion species, and total vanadium concentration, in a sample. A sample suspected of containing vanadium in one or more of these oxidation states is combined with a colorimetric substrate that will provide for different absorption spectra with vanadyl and vanadate complexes. Suitable colorimetric substrates include halogenated hydroxyquinolines, e.g. broxyquinoline (DBHQ). The solvent and assay conditions are chosen to minimize oxidation of the vanadium. The absorbance of the sample is then read at two wavelengths, one that indicates the presence of both vanadyl and vanadate, and one that indicates the presence only of one species, generally vanadate. By comparison to a standard curve, the total concentration and the species concentration of vanadium in the sample is determined.

14 Claims, 6 Drawing Sheets

Oxidation of KP-102 in isopropanol and ethanol

Oxidation of BEOV in McCoy's Media

SPECTROPHOTOMETRIC ASSAY FOR THE DETERMINATION OF TOTAL VANADIUM AND THE +IV AND +V OXIDATION STATES OF VANADIUM

This application claims benefit to Provisional Application Ser. No. 06/095,729 filed Aug. 7, 1998.

BACKGROUND OF THE INVENTION

TECHNICAL FIELD

This invention relates to the field of analytical chemistry, more specifically to the field of spectrophotometric analysis of the transition metal vanadium and its oxidation state in pharmaceutical preparations and biological samples.

Introduction

Vanadium is a trace metal with remarkable properties. It believed to be an essential nutrient for many species, including man. Vanadium is a pervasive element of biological systems, being widely distributed across the food supply. At higher intakes, it accumulates in body tissues such as liver, kidney and bone. Vanadium has been shown to be useful as a therapeutic agent; for chemoprotection against cancers in animals (Bishayee and Chatterjee (1995); Djordjevic (1995)) as well as to alleviate the symptoms of diabetes by acting as an insulin mimetic (Tolman et al. (1979); Heyliger et al. (1985); Meyerovitch et al. (1987)).

The oxidation state of vanadium influences the biodistribution. In fact, incorporated vanadium appeared to be exclusively in the vanadyl (4+ oxidation state) form, and not the vanadate (5+ state). On examination of vanadyl ion in vitro, Sakurai et al. (1995) *Biochem Biophys Res Commun* 206(1):133–137, found that incubation of DNA with vanadyl ion and hydrogen peroxide ($H_2O_2$) led to intense DNA cleavage, and proposed that the mechanism for vanadium-dependent toxicity as well as its antineoplastic action was due to DNA cleavage by hydroxyl radicals. The data suggests that vanadyl compounds are less toxic than vanadate. However, vanadium is highly susceptible to oxidation under ordinary conditions. Crans et al. (1995) studied the stability of vanadium compounds. Several compounds including those currently favoured as insulin-mimetic agents were unstable in distilled water at pH 7. Even well characterized vanadium compounds were surprisingly labile.

On the basis of a number of studies (for example, see Erdmann et al. (1984); Nakai et al. (1995)), the vanadyl state has been proposed to be the active form of vanadium for insulin mimetic action, and is responsible for the positive actions of vanadium in vivo. At the same time, because vanadium tends to oxidize very easily, making stable and safe preparations of vanadium therapeutics is a challenge. It is therefore important to determine the oxidative state of vanadium before and after pharmaceutical administration.

Relevant Literature

Various kinds of samples have been analyzed for trace amounts of vanadium as a biological nutrient (Hurley in Trace Element Analytical Chemistry in Medicine and Biology, ed. Bratter et al., Berlin, 1984, vol. 3, p. 375), epidemiological preventive (Mracova et al., Science Total Environ, 1993, part 1, E16/633), pollutant (Langard S., and Norseth, T., in Handbook on the Toxicology of Metals, ed. Friberg, L, Nordberg, G F, and Vouk, V B., Elsevier, Amsterdam, 1986), and occupational hazard (Occupational Diseases—A guide to their recognition. ed. Key et al., U.S. Department of Health, Education and Welfare, U.S. Government Printing Office, Washington D.C., June 1977).

Spectroscopic studies of oxovanadium (IV) complexes of biguanide, dibiguinide and 0-methyl-1-amidinourea were performed by Syamal (1983) Ind. J. Pure & Applied Physics 21:130–132. ESR, IR and electronic spectra were recorded. Indirect determination of vanadium may be performed by atomic absorption spectrometry (Chakraborty et al. (1989)).

In Keller et al. (1991) complexes of vanadyl, were reported to be formed with the trihydroxamic acid deferoxamine (H3DF+) with one complex exhibiting a characteristic reddish-violet color with a major absorbance peak at 386 nm and a smaller peak at 520 nm. In Rodriguez et al. (1994), oxyvanadium was reacted with molybdic acid in the presence of phosphate to form molybdivanadophosphoric acid absorbing at 385 nm and yellow in colour. In Bajeva et al. vanadate was reacted with N-m-tolyl-p-methoxy benzohydroxamic acid to form a 1:2 (metal to ligand) complex containing a basic V=O group and an acidic V—OH group, which formed addition compounds with thiocyanate to give a hyper- and bathochromic effect in chloroform. On the basis of this bathochromic effect of thiocyanate the spectrophotometric determination of vanadate was possible, in that the blue colored complex of vanadate could be extracted in chloroform, and had an absorption maxima at 580 nm.

Elvingson et al. (1996) speciated vanadium maltol in saline using NMR, ESR and potentiometric techniques. Takaya and Sawatari (1994) *Ind. Health* 32:165–178, speciated vanadium using ion-exchange chromatography and ICP-AES.

Ahmed and Banerjee provided a method for the spectrophotometric determination of vanadate using 5,7-dibromo-8-hydroxyquinoline (DBHQ) in slightly acidic solution. They attempted to distinguish between vanadyl and vanadate by masking vanadyl using tartrate and measuring absorbance at 400 nm in ethanol.

SUMMARY OF THE INVENTION

Methods are provided for the simultaneous quantitation of the (+IV) vanadyl and (+V) vanadate oxidation forms of vanadium. A sample is combined with a colorimetric substrate that forms a complex with the vanadium species, and which complexes differentially absorb light when formed with vanadyl or with vanadate. The buffers in the assay are chosen to minimize oxidation of the vanadium during the assay procedure. The methods are particularly useful for monitoring the oxidation of vanadyl to vanadate during manufacturing, pharmaceutical administration, etc. Oxidation may be determined at a single point, or over a time course, e.g. under conditions suspected of causing vanadyl oxidation. In a preferred embodiment, the colorimetric substrate is 5,7-dibromo-8-quinolinol (broxyquinoline), which provides for differential absorption of vanadyl at 400 nm and 525 nm.

DETAILED DESCRIPTION OF THE INVENTION

Figure 1:
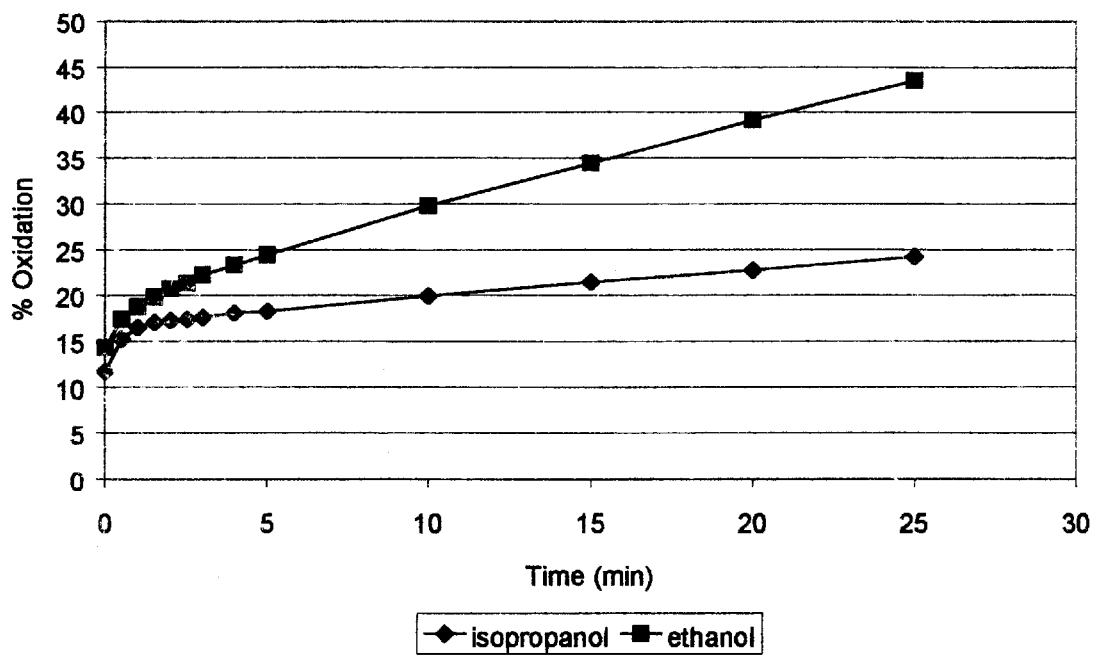
FIG. 1 is a graph depicting the oxidation of BEOV (KP-102) in isopropanol and ethanol.
Figure 2A:
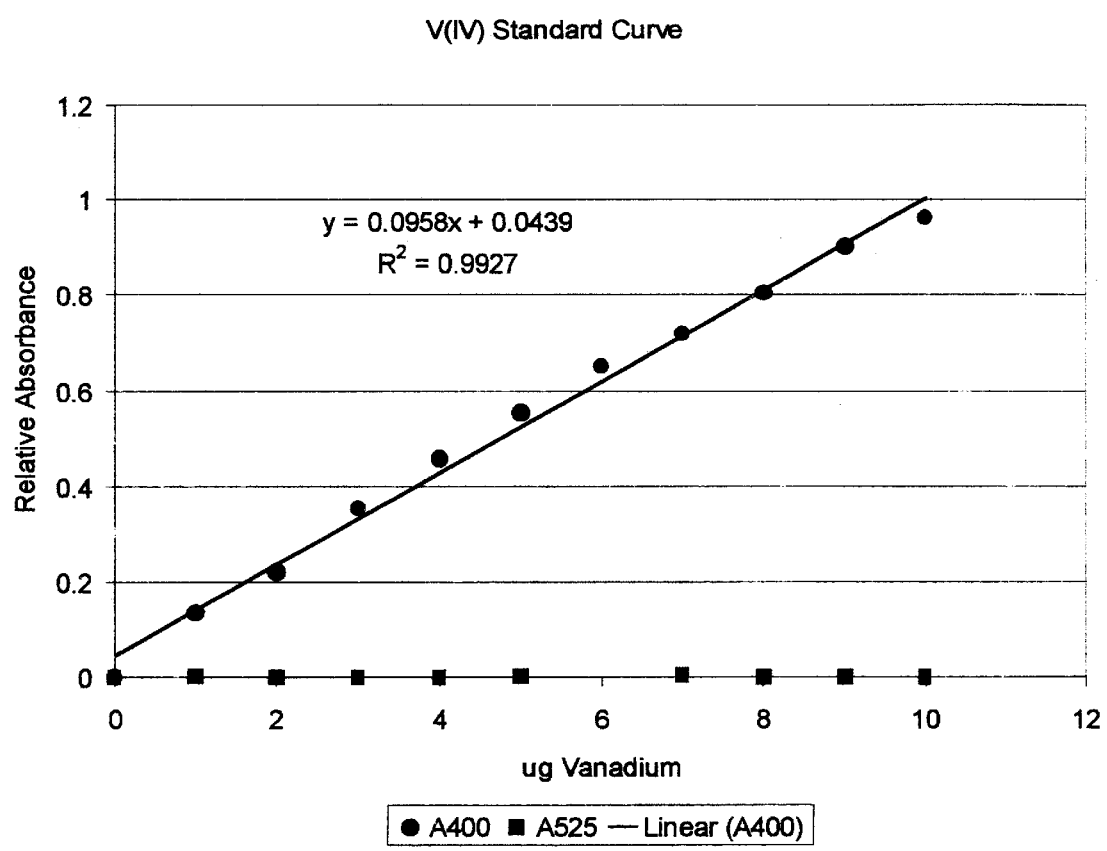
FIG. 2A is a graph depicting the standard curve of vanadium (IV).
Figure 2B:
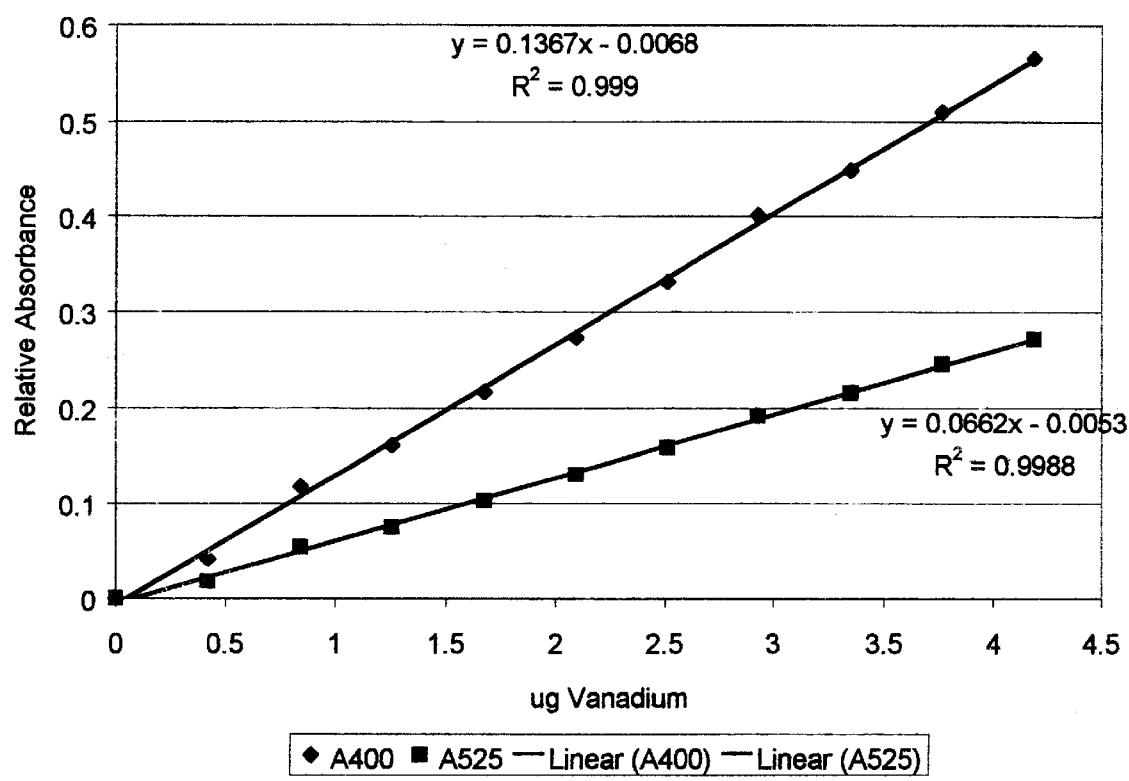
FIG. 2B is a graph depicting the standard curve of vanadium (V).

A colorimetric assay is provided for determining the vanadium species, and total vanadium concentration, in a sample. Two of the biologically relevant vanadium species, vanadyl (+IV) and vanadate (+V), differ significantly in their pharmacological activity, yet many compounds convert from vanadyl to vanadate under physiological conditions. The invention provides a simple determination of vanadyl oxidation.

A sample suspected of containing vanadium in one or more oxidation states is combined with a colorimetric substrate that will provide for different absorption spectra with vanadyl and vanadate. Suitable colorimetric substrates include halogenated hydroxyquinolines, e.g. broxyquinoline (DBHQ). The solvent and assay conditions are chosen to minimize oxidation of the vanadium. The absorbance of the sample is then read at two wavelengths, one that indicates the presence of both vanadyl and vanadate, and one that indicates the presence only of one species, generally vanadate. By comparison to a standard curve, the total concentration and the species concentration of vanadium in the sample is determined.

Colorimetric assay methods are relatively quick and easy to perform, provide the researcher with a quantitative assay of the vanadium species, provide corroborative data to other physical methods, and provide insight into the behavior of the molecule under a variety of conditions which might be cumbersome to perform by other methods. Comparison of results obtained by the methods of the invention compared favorably to current methods but with the added benefit of differentiation between different valencies of vanadium. The methods, and kits for the practice of the method, are technically simple, requiring no onerous procedures or radiolabel detection and are therefore quick to perform and relatively low in cost.

The methods of the invention are useful in the preparation, qualification of pharmaceutical preparations of vanadium. The methods are also useful in the development of vanadium formulations for therapeutic applications, in that a way to assess the level of oxidation of such compounds in the blood post administration is essential in determining bioavailability, and potentially in explaining toxicity.

Samples, as used herein, include any sample suspected of containing vanadium (IV) or vanadium (V), usually at a concentration ranging from 0 to about 10 $\mu$g/ml. While many samples will comprise vanadium in solution, solid samples that can be dissolved in a suitable solvent may also be assayed. Samples of interest include environmental samples, e.g. ground water, sea water, mining waste, etc.; biological samples, e.g. lysates prepared from crops, tissue samples, etc.; manufacturing samples, e.g. time course during preparation of pharmaceuticals comprising vanadyl, etc.; and the like.

Samples of particular interest include biological fluids such as blood, saliva, lymph, dialysis fluid and the like; organ or tissue culture derived fluids; and fluids extracted from physiological tissues. Also included in the term are derivatives and fractions of such fluids, including serum or plasma, with or without dilution. Where the assay samples comprise blood samples, the use of plasma or serum is preferred, alternatively NaF may be added to mask the presence of Fe in the red blood cell component of blood.

The term samples also includes the fluids described above to which additional components have been added, for example components that affect the ionic strength, pH, total protein concentration, etc. In addition, the samples may be treated to achieve at least partial fractionation or concentration. Biological samples may be stored if care is taken to reduce oxidation, e.g. under nitrogen, frozen, or a combination thereof.

The volume of sample used is sufficient to allow for measurable colorimetric detection, usually from about 0.1 $\mu$l to 1 ml, more usually from about 1 $\mu$l to about 500 $\mu$l of a biological sample is sufficient.

Samples may be taken from a single point in time, or a series of samples may be used in order to monitor the oxidation of vanadyl under a particular set of conditions. It is anticipated that an important use of the invention will be in monitoring the stability of pharmaceutical vanadium compositions to oxidation under particular manufacturing and storage conditions.

Samples, fractions or aliquots thereof are then diluted into an assay buffer in separately assayable containers, for example, separate wells of a microtiter plate, test tubes, etc. The invention may be used with or without standards as references. Where used, separate standards preferably contain vanadyl and vanadate ions of known concentration. The concentration ranges of the standards will provide references for at least the range of values expected from the test samples. In general the range is found between about 1 $\mu$g/ml and 100 $\mu$g/ml, usually not more than about 10 $\mu$g/ml. Preferably, a series of standards, containing known concentrations, is assayed in parallel with the samples or aliquots thereof to serve as controls. Each sample and standard will generally be added to multiple wells so that mean values can be obtained for each.

The dilution of the sample into an assay buffer that minimizes vanadyl oxidation is important for the success of the invention. Usually the dilution will be at least about 1:2, more usually at least about 1:5, preferably at least about 1:10, and may be higher where the vanadium concentration in the sample permits further dilution.

A preferred solvent for the assay is acidic isopropanol. Other solvents that minimize vanadyl oxidation include acidified alkanols, e.g. propanol, butanol, etc., benzene, toluene, ethers, and the like. Generally, ethanol will not be used as a buffer, due to high oxidation rates of the vanadium. In a preferred embodiment, the assay buffer will be prepared with the colorimetric substrate prior to dilution of the sample.

The colorimetric substrate forms a colored complex with vanadyl and vanadate, where the products formed from the two species have different absorption spectra. Reagents of particular interest are halogenated hydroxyquinolines, of the formula:

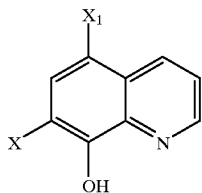

where X and $X_1$ are, independently, halogen substituents, e.g. bromine, chlorine, iodine, etc. A preferred substrate is 5,7dibromo-8-hydroxyquinoline (broxyquinoline, DBHQ).

The substrate will be present in a molar excess relative to the vanadium present in a sample, usually at least about a one log excess, more usually at least about two logs, and usually about three or more logs excess. For the assay of biological or environmental samples, where only trace levels of vanadium will be present, the substrate will be present at a concentration of from about 0.1 mM to about 10 mM, usually at a concentration of from about 1 mM to 5 mM, more usually at about 3 mM. When the samples are from manufacturing, where vanadium concentrations are higher, the substrate may be used at a higher concentration, or the sample diluted to appropriate levels.

The absorbance of the sample is then read at two wavelengths, one that provides a measure of both vanadate and vanadyl, and one that provides a measure of only one ion, usually the vanadate ion. The absorption spectra can be determined by scanning a test sample over a series of wavelengths to determine the optima. Where the colorimetric substrate is broxyquinoline, the preferred wavelengths are 400 nm for a reading of total vanadium, and 525 nm for a reading of vanadate alone. The vanadium (IV) complex in buffer displays significant absorbance at 400 nm while the vanadium (V) complex in buffer displays significant absorbance at both 400 and 525 nm.

In order to minimize oxidation of vanadyl, it is desirable to minimize the period of time between addition of the sample to the colorimetric substrate, and reading the absorbance, usually at least about 5 s. and not more than about 5 minutes, more usually at least about 15 s. and not more than about 1 minute.

For some biological samples, particularly those having high concentration of protein present, e.g. plasma, medium containing serum, etc., it may be desirable to remove precipitate prior to reading the absorbance. Any convenient method, as known in the art, may be used for this purposes, e.g. spin columns, centrifugation, etc.

The invention can be practiced qualitatively or quantitatively. In a qualitative assay, the vanadium concentrations of the samples, mixtures, or fractions thereof are defined relative to one another or to the concentrations of other non-standardized vanadium samples. In a quantitative assay, all vanadium concentrations are related to a series of standards of known concentration. Accordingly, absolute (weight/volume) concentration values can be obtained. To accurately quantify the data, the series of standards generally fall within a range limitation imposed by the method of measurement.

For quantitative assays, the absorbance value for each standard may be plotted against the vanadium (vanadyl and/or vanadate) concentrations on graph paper and a standard curve constructed with absorbance on the linear y axis and vanadium concentration (mg/ml) on the x axis. The vanadium concentrations of the individual samples may then be read off the plot.

Alternatively, the quantitation is calculated as follows. The extinction coefficient ($\epsilon$) for vanadium (IV) is calculated as:

$$\epsilon_{400(IV)} = \text{Absorbance 400 nm/Concentration vanadium (IV)} = A_{400}/C_{(IV)}$$

The extinction coefficients for vanadium (V) are:

$$\epsilon_{400(V)} = A_{400}/C_{(V)}$$
$$\epsilon_{525(V)} = A_{525}/C_{(V)}$$

Therefore for unknown samples:

concentration $V(V) = A_{525}/\epsilon_{525(V)} = \mu g$ Vanadium (V)/ml assay buffer concentration $V(IV) = (A_{400}/\epsilon_{400(IV)}) - [(\epsilon_{400(V)} A_{525})/(\epsilon_{400(IV)} \epsilon_{525(V)})] = \mu g$ Vanadium (IV)/ml assay buffer concentration $V\text{total} = V(V) + V(IV)$ It is contemplated that a kit will be provided for convenient performance of the invention. Such a kit will comprise the colorimetric substrate, which may be individually packaged for multiple assays, the assay solvent, and vanadium for standards. The vanadyl and vanadate are generally provided separately, and may be provided in dry aliquots, so that one need only add a predetermined volume of solvent in order to use the standards. Optionally, such a kit will further comprise such tubes, pipettes and other disposable labwear necessary for the practice of the method.

Experimental

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

Materials (Bis(ethylmaltolato)oxovanadium (IV); BEOV), lot number 2462-AL-1P, Raylo Chemicals Inc, Edmonton, Alberta Canada, was prepared as a 3 mg/ml solution in deionized water. The solution was stored under nitrogen atmosphere in vacutainer tubes until used. (Bis(ethylmaltolato)dioxovanadium (V); BEOV(V) was manufactured at Kinetek Pharmaceuticals, Inc.

100 mM Sodium Phosphate Buffer, pH 7.4 was prepared by mixing 70 ml of 1 M $NaH_2PO_4.H_2O$ with 430 ml of 1 M $Na_2HPO_4$. The 1 M stocks were prepared by dissolving 13.8 g $NaH_2PO_4.H_2O$ (lot #966803, Fisher Scientific Company) in 100 ml sterile distilled $H_2O$ or 71.0 $Na_2HPO_4$ (lot #976512, Fisher Scientific Company) in 500 ml of sterile distilled $H_2O$.

Fischer's medium, lot #T-589, Quality Biological Inc., containing 5% horse serum and Mc Coy's 5a medium, Mediatech Inc., were supplied by Covance Laboratories Inc., Vienna, Va., USA. Fetal bovine serum, lot #01087, was purchased from Biochemed Corp, Winchester, Va., USA.

5,7-dibromo-8-hydroxyquinoline (DBHQ), lot #62C2050, was purchased from Sigma Chemical Corporation, St. Louis, Mo. USA. Sodium metavanadate (vanadium (V)), lot #4871150H, was purchased from BDH Chemicals, Ltd., Poole, England. Vanadium (IV) standard, lot #87H3498, was purchased from Sigma Chemical Company, St. Louis, Mo., USA. Isopropanol, lot #37064 was purchased from VWR. Sulfuric acid, lot #196305 was purchased from Fisher Scientific Co.

Preparation of Reagents Required for Standard Curve and Testing Levels of Vanadium(IV) and Vanadium(V).

Preparation of 3 mM 5,7-dibromo-8-hydroxyquinoline (DBHQ) solution is done by dissolving 9.09 mg DBHQ in 10 ml ethanol or isopropanol. The mixture may need to be heated to dissolve the DBHQ. If isopropanol is used, the DBHQ will precipitate over time but reheating will redissolve it.

Sulfuric acid ($H_2SO_4$) 75 mM is prepared by adding 6 ml 2.5 N $H_2SO_4$ to 100 ml water. Isopropanol is used at full strength (100%).

Standards. The atomic absorption standard is purchased from Sigma Chemical Co., St. Louis, Mo.

Vanadate Standard, sodium metavanadate (NaVO3) 1 mg/ml is prepared by adding to 100 mg $NaVO_3$ in 99 ml water up to 1 molar concentrated nitric acid. The solution turns yellow upon addition of the nitric acid, and an orange precipitate may form, which should be dissolved with stirring.

Vanadyl Standard, vanadium atomic absorption standard at 1 mg/ml should have zero absorbance at 525 nm. The vanadyl standard will oxidize in the presence of the assay reagents, therefore, standards and samples should be read immediately after mixing.

Data Analysis/Calculation

The vanadium (IV):DBHQ complex in isopropanol displays significant absorbance at 400 nm while the vanadium (V):DBHQ complex in isopropanol displays significant absorbance at both 400 and 525 nm.

The extinction coefficient ($\epsilon$) for Vanadium (IV) is:

$$\epsilon_{400(IV)} = \text{Absorbance 400 nm/Concentration Vanadium (IV)}$$

or $$\epsilon_{400(IV)} = A_{400}/C_{(IV)}$$

The extinction coefficients for Vanadium (V) are:

$$\epsilon_{400(V)} = A_{400}/C_{(V)}$$

$$\epsilon_{525(V)} = A_{525}/C_{(V)}$$

Therefore for unknown samples:

$$V(V) = A_{525}/\epsilon_{525(V)} = \mu g \text{ Vanadium (V)/ml assay eluent}$$

$$V(IV) = A_{400}/\epsilon_{400(IV)} - [(\epsilon_{400(V)}A_{525})/(\epsilon_{400(IV)}\epsilon_{525(V)})] = \mu g \text{ Vanadium (IV)/ml assay eluent}$$

$$V_{total} = V(V) + V(IV)$$

BEOV ($\mu$g BEOV/ml assay mixture) is calculated as:

$$\mu g \text{ BEOV/ml} = [\text{BEOV Molecular Wt/Vanadium Molecular Wt}]$$

$$(V_{total}) = (345/51)(V_{total}(\text{in mg/mL assay mixture}))$$

The percent oxidation is determined as:

$$\% \text{ oxidation} = 100[V(V)/(V(V)+V(IV))]$$

Preparation of Standard Curve

The following procedure should be performed in clean, disposable glass tubes. To make 100 ml of assay solution mix the stocks above as indicated below. Scale up or down as necessary leaving the relative amounts of each component unaltered.

Assay Solution

In a flask 18 mg DBHQ was dissolved in 40 ml of isopropanol or ethanol with warming followed by the addition of 60 ml of isopropanol and 100 $\mu$l of concentrated sulfuric acid. The solution (DBHQ assay reagent) was allowed to cool to room temperature prior to use. The assays are performed on 100 $\mu$l to 400 $\mu$l of aqueous sample in a total of 1 ml of aqueous sample plus isopropanol, so that the isopropanol is at a concentration of 90–60%.

Alternatively, 20 ml of 3 mM DBHQ in isopropanol, 100 $\mu$l concentrated $H_2SO_4$, 50 ml isopropanol and 20 ml $H_2O$ were mixed together in a clean beaker or flask. The DBHQ should not precipitate from the assay solution.

Standard Solutions

Standards for vanadate and vanadyl were prepared using from 0 to 10 $\mu$l of vanadate standard and vanadyl standard solutions placed in tubes labeled according to the concentration of sample solution, namely 0, 1, 2, 3, etc., up to 10. Water was added to a final volume of 100 to 400 $\mu$l depending on the amount of unknown sample anticipated and assay reagent was added to a final volume of 1 ml. The assay was run on 5 $\mu$l and 10 $\mu$l aliquots of solutions.

About 1 ml total volume was measured per sample in quartz cuvettes using an ULTRASPEC(r) 3000 (Pharmacia Biotech) at 525 nm and 400 nm simultaneously.

Each tube was shaken gently for about 15 seconds and the absorbance at 400 nm and 525 nm was recorded between 30 to 60 seconds later. The tubes were assayed one at a time in this manner as prolonged exposure to the assay conditions will result in oxidation of the standard.

The vanadium (IV) standard did not exhibit a significant absorbance at 525 nm. The DBHQ:vanadyl complex absorbs only at 400 nm. The vanadate standard:DBHQ complex absorbed at 400 nm and 525 nm. The absorbance of vanadate at 525 nm was about 0.47 times than that at 400 nm in isopropanol and almost 0.6 times that at 400 nm in ethanol.

Extinction coefficients ($\epsilon$) are determined from the standard curves by dividing the absorbance (A) by the concentration (C) of vanadium in $\mu$g/ml. The extinction coefficients for the vanadate standard were calculated for the absorbance at 400 nm and at 525 nm.

EXAMPLE 1

Oxidation of BEOV in Assay Reagent Made from Ethanol and Isopropanol

The purpose of this experiment was to compare the oxidation rates of vanadium (as a solution of BEOV) in ethanol and isopropanol. It was found that oxidation occurred in the assay medium. The rate of oxidation was greater in ethanol than in isopropanol.

For this experiment, an aliquot of BEOV was added to the bottom of a 13×100 mm tube. To the BEOV and water in the tube was added 1 ml of DBHQ assay reagent in acidic ethanol or isopropanol prepared according to method 1 under "Assay Solution". The tube containing assay reagent and BEOV was agitated for 15 seconds to allow for color development, and then the contents of the tube were transferred to a 1.5 ml quartz cuvette. The absorbance of the solution at 400 nm and 525 nm was monitored within the same cuvette over time. The results are shown in FIG. 1.

EXAMPLE 2

Standard Curves for Vanadium in Isopropanol

Standards of V(IV) and V(V) were prepared as described and assayed in 1 ml of DBHQ assay reagent in acidic isopropanol prepared according to method 1 under "Assay Solution". The tube containing assay reagent and standard was agitated for 15 seconds to allow for color development, and then the contents of the tube were transferred to a 1.5 ml quartz cuvette. The standards were aliquoted and the results were obtained according to the following table and figures:

TABLE 1 atomic absorption standard; V(IV) Std.

| Tube | $\mu$g V | $A_{400}$ | $A_{525}$ | $e_{400}$ |
|---|---|---|---|---|
| 1 | 0 | 0 | 0 | |
| 2 | 2 | 0.249 | 0.002 | 0.1245 |
| 3 | 4 | 0.453 | 0.004 | 0.11325 |
| 4 | 6 | 0.671 | 0.006 | 0.111833 |
| 5 | 8 | 0.811 | 0.008 | 0.101375 |
| 6 | 10 | 0.927 | 0.008 | 0.0927 |
| | | | Average | 0.108732 | sodium metavanadate; V(V) standard

| Tube | $\mu$l | $\mu$g V | $A_{400}$ | $A_{525}$ | $e_{400}$ | $e_{525}$ |
|---|---|---|---|---|---|---|
| 1 | 0 | 0 | 0.003 | 0.001 | | |
| 2 | 2 | 0.836546 | 0.115 | 0.051 | 0.13747 | 0.060965 |
| 3 | 4 | 1.673091 | 0.221 | 0.109 | 0.132091 | 0.065149 |
| 4 | 6 | 2.509637 | 0.334 | 0.161 | 0.133087 | 0.064153 |
| 5 | 8 | 3.346182 | 0.443 | 0.215 | 0.13239 | 0.064252 |
| 6 | 10 | 4.182728 | 0.571 | 0.277 | 0.136514 | 0.066225 |
| | | | | Average | 0.13431 | 0.064149 |

The V(IV) standard curve illustrates that there is no appreciable absorption at 525 nm.

EXAMPLE 3

Measurement of the Oxidation of BEOV in Cell Culture Media

This study evaluated the stability of BEOV (bis (ethylmaltolato)oxovanadium(IV)) in various cell culture media. The rate of oxidation in Fischer's media and McCoy's media was monitored over time.

Figure 3:
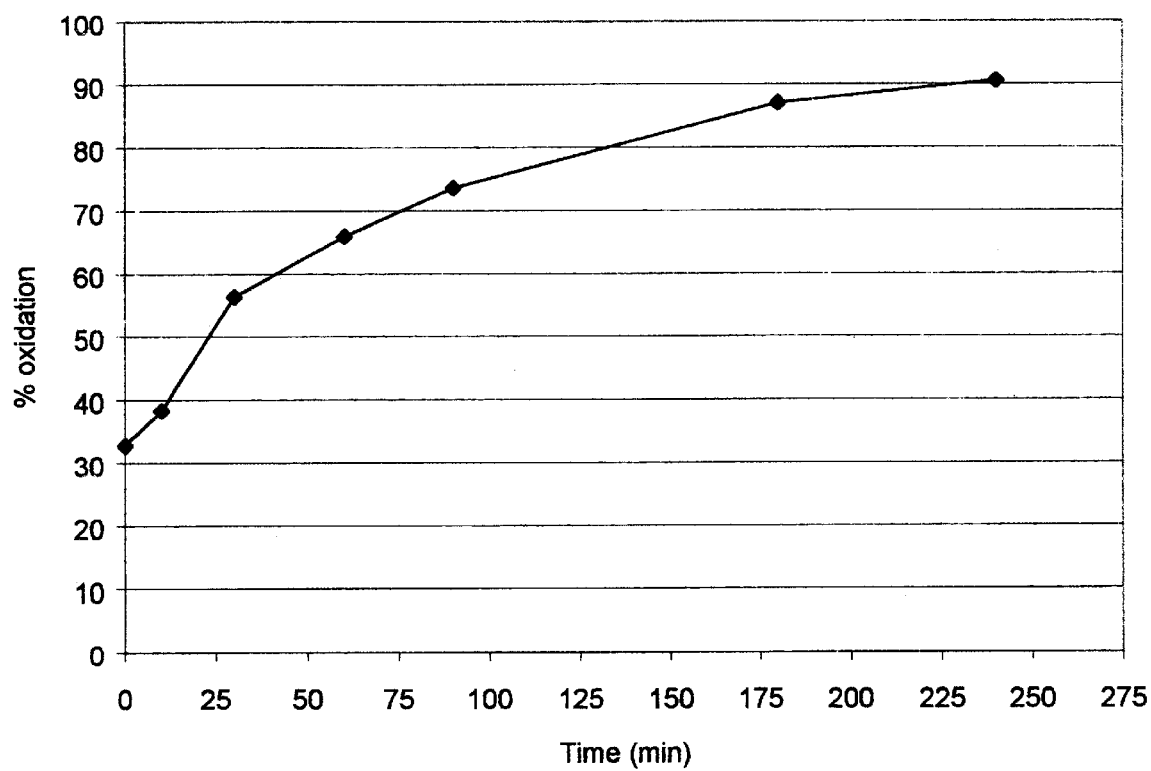
FIG. 3 is a graph depicting oxidation of BEOV in Fischer's medium.
Figure 4:
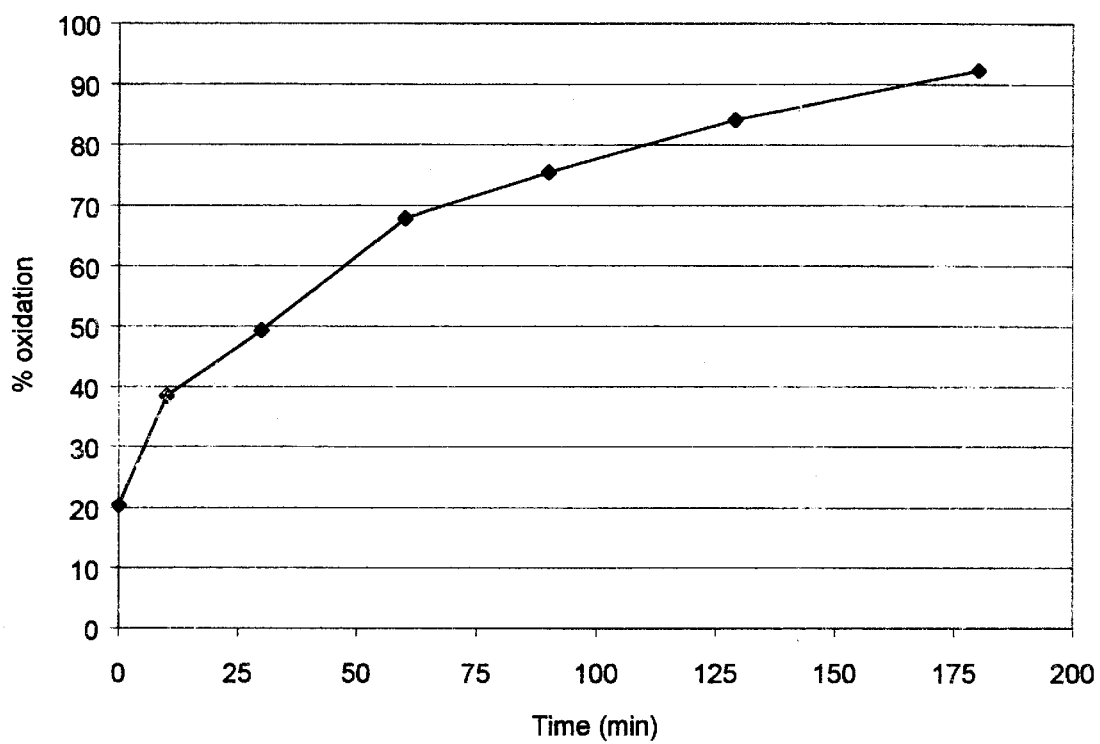
FIG. 4 is a graph depicting the oxidation of BEOV in McCoy's medium.

Assay in Fischer's media: 0.95 ml of BEOV at 3 mg/ml in water was added to 9 ml of media. The medium was incubated at 37 C. or an orbital shaker at 80 rpm. The data and extinction coefficients are presented in the following tables, and in FIG. 3.

TABLE 2

Standard Curves

| V(IV), $\mu$g | A400 | A525 | e400 | | |
|---|---|---|---|---|---|
| 0 | 0 | 0 | | | |
| 1 | 0.133 | 0.03 | 0.133 | | |
| 2 | 0.223 | 0.023 | 0.1115 | | |
| 3 | 0.36 | 0.033 | 0.12 | | |
| 4 | 0.459 | 0.052 | 0.11475 | | |
| 5 | 0.568 | 0.06 | 0.1136 | | |
| 6 | 0.67 | 0.102 | 0.111667 | | |
| 7 | 0.856 | 0.093 | 0.122286 | | |
| 8 | 0.919 | 0.09 | 0.114875 | | |
| 9 | 1.029 | 0.112 | 0.114333 | | |
| 10 | 1.226 | 0.274 | 0.1226 | | |
| | | Average | 0.117861 | | |

| V(V), $\mu$l | $\mu$g V(V) | A400 | A525 | e400 | e525 |
|---|---|---|---|---|---|
| 0 | 0 | 0 | 0 | | |
| 1 | 0.418273 | 0.038 | 0.018 | 0.09085 | 0.043034 |
| 2 | 0.836546 | 0.103 | 0.048 | 0.123125 | 0.057379 |
| 3 | 1.254818 | 0.16 | 0.079 | 0.127508 | 0.062957 |
| 4 | 1.673091 | 0.194 | 0.09 | 0.115953 | 0.053793 |
| 5 | 2.091364 | 0.252 | 0.115 | 0.120496 | 0.054988 |
| 6 | 2.509637 | 0.316 | 0.148 | 0.125915 | 0.058973 |
| 7 | 2.927909 | 0.369 | 0.17 | 0.126028 | 0.058062 |
| 8 | 3.346182 | 0.401 | 0.187 | 0.119838 | 0.055885 |
| 9 | 3.764455 | 0.443 | 0.203 | 0.11768 | 0.053925 |
| 10 | 4.182728 | 0.451 | 0.203 | 0.107824 | 0.048533 |
| | | | Average | 0.117522 | 0.054753 |

TABLE 3

Time Course in Fischer's Media

| Time (min) | A400 | A525 | A400 | A525 | A400 | A525 | V(V) | V(IV) | % oxidized |
|---|---|---|---|---|---|---|---|---|---|
| 0 | 0.555 | 0.078 | 0.595 | 0.097 | 0.575 | 0.0875 | 1.59 | 3.28 | 32.7261 |
| 10 | 0.627 | 0.112 | 0.627 | 0.111 | 0.627 | 0.1115 | 2.03 | 3.29 | 38.2377 |
| 30 | 0.599 | 0.15 | 0.642 | 0.176 | 0.6205 | 0.163 | 2.98 | 2.30 | 56.4550 |
| 60 | 0.632 | 0.192 | 0.633 | 0.197 | 0.6325 | 0.1945 | 3.55 | 1.82 | 66.0687 |
| 90 | 0.59 | 0.199 | 0.633 | 0.221 | 0.6115 | 0.21 | 3.83 | 1.36 | 73.76718 |
| 180 | 0.581 | 0.234 | 0.598 | 0.244 | 0.5895 | 0.239 | 4.36 | 0.65 | 87.05384 |
| 240 | 0.568 | 0.239 | 0.653 | 0.276 | 0.6105 | 0.2575 | 4.70 | 0.49 | 90.55689 |

Assay in McCoy's media: 1 ml of BEOV at 3 mg/ml in water was added to 9 ml of media. The medium was incubated at 37 C. in an incubator at 5% $CO_2$ in air. The raw and extinction coefficients are presented in the following tables.

TABLE 4

Standard Curves in McCoy's Media

| V(IV), µg | A400 | A525 | e400 |
|---|---|---|---|
| 0 | 0 | 0 | |
| 1 | 0.058 | 0.012 | 0.058 |
| 2 | 0.237 | 0.029 | 0.1185 |
| 3 | 0.351 | 0.055 | 0.117 |
| 4 | 0.576 | 0.118 | 0.144 |
| 5 | 0.628 | 0.077 | 0.1256 |
| 6 | 0.653 | 0.032 | 0.108833 |
| 7 | 0.816 | 0.05 | 0.116571 |
| 8 | 1.138 | 0.184 | 0.14225 |
| 9 | 1.069 | 0.093 | 0.118778 |
| 10 | 1.181 | 0.092 | 0.1181 |
| | | Average | 0.116763 |

| V(V), µl | µg V(V) | A400 | A525 | e400 | e525 |
|---|---|---|---|---|---|
| 0 | 0 | 0 | 0 | | |
| 1 | 1.025806 | 0.158 | 0.074 | 0.154025 | 0.072138 |
| 2 | 2.051613 | 0.295 | 0.14 | 0.143789 | 0.068239 |
| 3 | 3.077419 | 0.433 | 0.206 | 0.140702 | 0.066939 |
| 4 | 4.103226 | 0.568 | 0.269 | 0.138428 | 0.065558 |
| 5 | 5.129032 | 0.699 | 0.331 | 0.136283 | 0.064535 |
| 6 | 6.154839 | 0.842 | 0.398 | 0.136803 | 0.064665 |
| 7 | 7.180645 | 0.99 | 0.466 | 0.137871 | 0.064897 |
| 8 | 8.206452 | 1.241 | 0.58 | 0.151222 | 0.070676 |
| 9 | 9.232258 | 1.25 | 0.583 | 0.135395 | 0.063148 |
| 10 | 10.25806 | 1.368 | 0.636 | 0.133358 | 0.062 |
| | | | Average | 0.140788 | 0.066279 |

Note: Standard curve for V(V) used BEOOV (the V(V) version of BEOV).

| Time (m.) | A400 | A525 | A400 | A525 | A400 | A525 | V(V) | V(IV) | % oxidized |
|---|---|---|---|---|---|---|---|---|---|
| 0 | 0.588 | 0.071 | 0.565 | 0.057 | 0.5765 | 0.064 | 0.96 | 3.77 | 20.37722 |
| 10 | 0.683 | 0.135 | 0.633 | 0.131 | 0.658 | 0.133 | 2.00 | 3.21 | 38.42355 |
| 30 | 0.672 | 0.166 | 0.672 | 0.176 | 0.672 | 0.171 | 2.57 | 2.64 | 49.3834 |
| 60 | 0.746 | 0.249 | 0.739 | 0.253 | 0.7425 | 0.251 | 3.78 | 1.79 | 67.86929 |
| 90 | 0.603 | 0.216 | 0.696 | 0.266 | 0.6495 | 0.241 | 3.63 | 1.17 | 75.52596 |
| 129 | 0.635 | 0.251 | 0.744 | 0.311 | 0.6895 | 0.281 | 4.23 | 0.792 | 84.23993 |
| 180 | 0.731 | 0.316 | 0.742 | 0.333 | 0.7365 | 0.3245 | 4.89 | 0.40 | 92.37124 |

| | | | | | Average | | | | |
|---|---|---|---|---|---|---|---|---|---|
| Time (m.) | A400 | A525 | A400 | A525 | A400 | A525 | V(V) | V(IV) | % oxidized |
| 0 | 0.588 | 0.071 | 0.565 | 0.057 | 0.5765 | 0.064 | 0.96 | 3.77 | 20.37722 |
| 10 | 0.683 | 0.135 | 0.633 | 0.131 | 0.658 | 0.133 | 2.00 | 3.21 | 38.42355 |
| 30 | 0.672 | 0.166 | 0.672 | 0.176 | 0.672 | 0.171 | 2.57 | 2.64 | 49.3834 |
| 60 | 0.746 | 0.249 | 0.739 | 0.253 | 0.7425 | 0.251 | 3.78 | 1.79 | 67.86929 |
| 90 | 0.603 | 0.216 | 0.696 | 0.266 | 0.6495 | 0.241 | 3.63 | 1.17 | 75.52596 |
| 129 | 0.635 | 0.251 | 0.744 | 0.311 | 0.6895 | 0.281 | 4.23 | 0.792 | 84.23993 |
| 180 | 0.731 | 0.316 | 0.742 | 0.333 | 0.7365 | 0.3245 | 4.89 | 0.40 | 92.37124 |

EXAMPLE 4

Determination of BEOV and Oxidation State in Plasma

A standard of BEOV (V(IV)) was prepared in water. 200 µl of rat plasma was added to glass culture tubes containing aliquots of the vanadium standards. 1760 µl of DBHQ assay reagent and 40 µl of 5% sodium fluoride was added to each tube. Sodium fluoride was added to mask iron in the plasma.

Figure 5:
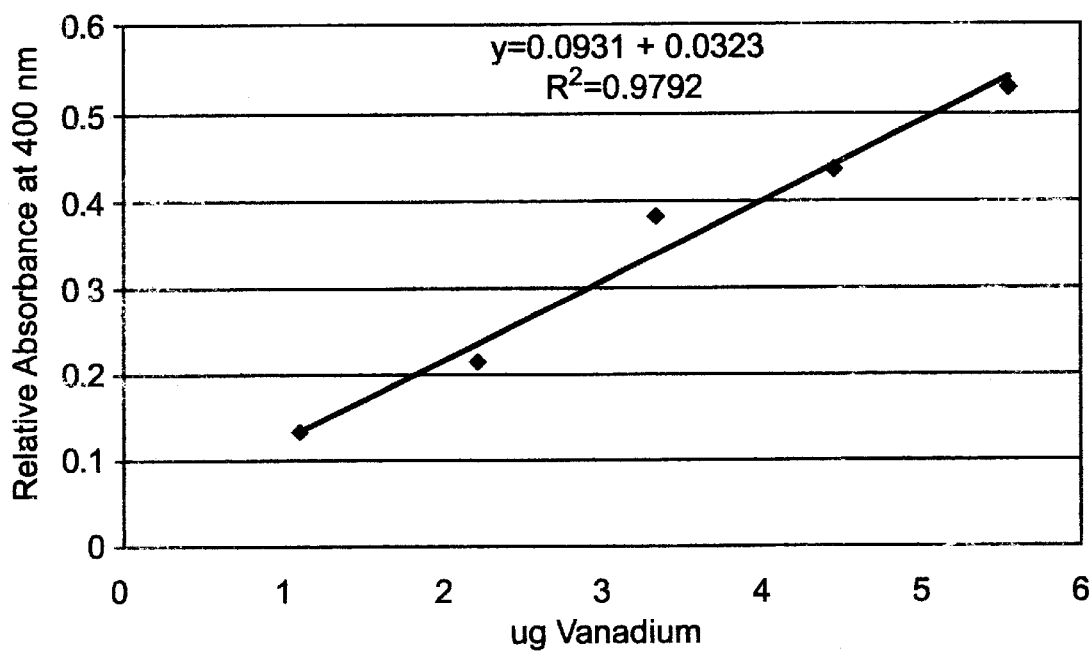
FIG. 5 is a graph depicting a standard vanadium (IV) curve in plasma.

To remove the plasma proteins that precipitate in the presence of the assay reagent, the solutions were filtered through 1 ml syringes stuffed with glass wool. The results are presented in the following table, and in FIG. 5.

TABLE 5

| | BEOV; V(IV) Standard (0.443 mg/ml) | | | |
|---|---|---|---|---|
| μl BEOV | μg V/ml | A400 | A525 | e400 |
| 5 | 1.1075 | 0.134 | −0.015 | 0.120993 |
| 10 | 2.215 | 0.215 | −0.011 | 0.097065 |
| 15 | 3.3225 | 0.381 | −0.007 | 0.114673 |
| 20 | 4.43 | 0.442 | −0.005 | 0.099774 |
| 25 | 5.5375 | 0.536 | 0.019 | 0.096795 |
| | | | Average | 0.10586 |

REFERENCES

Abu-Eittah and El-Nasr (1976) Spectrophotometric study of complex formation between oxovanadium (IV) and antiamebic drugs. Journal of Pharmaceutical Sciences. 65(9):1364–8.

Ahmed and Banerjee (1995) Non-extractive spectrophotometric determination of vanadium(v) in alloys and environmental, biological and soil samples using 5,7-dibromo-8-hydroxyquinoline. Analyst. 120(7):2019–23.

Amos and Sawyer (1974) Nuclear Magnetic Resonance Studies of 8-Quinolinol Complexes of Molybdenum (VI,V) and of Vanadium (V), as Models for Molybdenum-Flavin Interactions. Inorganic Chemistry 13 (1): 78–83.

Baveja A K., Gupta V K. (1984) Spectrophotometric determination of vanadium in complex materials using N-m-TMBHA and thiocyanate. International Journal of Environmental Analytical Chemistry. 17(3-4):299–306.

Bernheim F., Bernheim M L C. (1938) Action of vanadium on tissue oxidation. Science 88, 481–482.

Bishayee, A; and Chatterjee, M. (1995). Inhibitory effect of vanadium on rat carcinogenesis initiated by diethylnitrosamine and promoted by phenobarbital. Br. J. Cancer 71, 1214–20.

Bracken, W. M., and R. P. Sharma. (1985) Cytotoxicity-related alterations of selected cellular functions after in vitro vanadate exposure. Biochem. Pharmacol. 34: 2465–2470.

Chakraborty, D. Das, A K. (1989) Indirect determination of vanadium by atomic absorption spectrometry. Analytica Chimica Acta 218: 341–344.

Crans D C., Mahroof Tahir M., Keramidas A D.(1995) Vanadium chemistry and biochemistry of relevance for use of vanadium compounds as antidiabetic agents. Mol Cell Biochem 153(1–2):17–24

Djordjevic, C (1995) Antitumor activity of vanadium compounds. In. H. Sigel and A. Sigel (Eds) Metal Ions in Biological Systems. Vol 31, Vanadium and its role in Life, Marcel Dekker, New York, Basel, Hong Kong, pp. 595–616.

Domingo J L, Gomez M, Sanchez D J, Llobet J M, Keen C L; (1992) Tiron administration minimizes the toxicity of vanadate but not its insulin mimetic properties in diabetic rats. Life Sci 50:18 1311–7.

Domingo J L, Llobet J M, Tomas J M, Corbella J. (1986) Influence of chelating agents on the toxicity, distribution and excretion of vanadium in mice. J Appl Toxicol 6:5 337–41.

Domingo J L.(1996) Vanadium: a review of the reproductive and developmental toxicity. Reprod Toxicol 10:3 175–82.

Elberg G., Li J., Shechter Y. (1994) Vanadium activates or inhibits receptor and non-receptor protein tyrosine kinases in cell-free experiments, depending on its oxidation state. Possible role of endogenous vanadium in controlling cellular protein tyrosine kinase activity. J Biol Chem 269(13):9521–7.

Elvingson K; Baro, A G, Pettersson L. (1995) Speciation in vanadium bioinorganic systems. 2. An NMR, ESR and Potentiometric Study of the Aqueous H+-Vanadate-maltol system. Inorg. Chem. 35: 3388–3393.

Erdmann, E. (1980) Cardiac effects of vanadate. Basic Res. Cardiol. 75, 411–412.

French R J., Jones P J.,(1993) Role of vanadium in nutrition: metabolism, essentiality and dietary considerations. Life Sci 52(4):339–46.

Garner, M., Reglinski J., Smith W E. Et al. (1997) A 1 H spin echo and 51V NMR study of the interaction of vanadata with intact erythrocytes.

Hansen, T. V., J. Aaseth, and V. Skaug. (1985) Hemolytic activity of vanadyl sulphate and sodium vanadate. Acta Pharmacol Toxicol 59: 562–564.

Harland B F, Harden Williams B A.(1994) Is vanadium of human nutritional importance yet? J Am Diet Assoc 94(8):891–4

Hathcock, J. N., D. H. Hill, and G. Matrone. (1964) Vanadium toxicity and distribution in chicks and rats. J. Nutr. 86: 106–110.

Heyliger C E; Tahailiani A G; and McNeill J H (1985). Effect of vanadate on elevated blood glucose and depressed cardiac performance of diabetic rats. Science 227, 1474–1476.

Keller R J. Rush J D., Grover T A. (1991) Spectrophotometric and ESR evidence for vanadium(IV) deferoxamine complexes. Journal of Inorganic Biochemistry. 41(4):269–76.

Kiriyama T., Kuroda R. (1982) Combined ion exchange-spectrophotometric method for the simultaneous determination of vanadium and cobalt in biological materials. Analyst. 107(1274):505–10.

McNeill J H, Yuen, V G; Hoyveda H R; Orvig C (1992) Bis (maltolato) oxovanadium (IV) is a potent insulin mimic. J. Med. Chem. 35, 1489–91.

Meyerovitch, J; Farfel, Z; Sack J; Shechter Y (1987). Oral administration of vanadate normalizes blood glucose levels in streptozotocin-treated rats. J. Biol. Chem. 262, 6658–6662.

Mitchell, W. G. Influence of pH on toxicity of vanadium in mice. (1953) Proc. Soc. Exp. Biol. Med 84: 404–405.

Mitchell, W. G., and E. P. Floyd. (1954) Ascorbic acid and ethylene diamine tetraacetate as antidotes in experimental vanadium poisoning. Proc. Soc. Exp. Biol. Med 85: 206–208.

Nakai, M. Watanabe H; Fujiwara, C; Kadegawa, H., Satoh, T., Takada, J; Matsushita R and Sakurai H. (1995). Mechanism on insulin-like action of vanadyl sulfate: studies on interaction between rat adipocytes and vanadium compounds. Biol. Pharm. Bull. 18, 719–725.

Nechay et al. (1986) Vanadyl (IV) and vanadate (V) binding to selected endogenous phosphate, carboxyl, and amino ligands; calculations of cellular vanadium species distribution. Arch Biochem Biophys 251(1):128–38

Nielsen F H.(1991), Nutritional requirements for boron, silicon, vanadium,nickel, and arsenic: current knowledge and speculation. FASEB J 12, 5, 2661–7.

Novoa et al. (1982) Effect of sodium orthovanadate on renal renin secretion in vivo. J Pharmacol Exp Therap 222: 447–451.

Orvig et al. Vanadium compounds as insulin mimics, in Metal Ions Biol Syst. 31,Ed. Helmet Sigel & Astrid Sigel. Marcel Dekker Inc, 1995. Pp. 575–594.

Ramanadham et al. (1990) Enchanced in viov sensitivity of vanadyl-treated diabetic rats to insulin. Can. J. Physiol. Pharmacol. 68: 486–491.

Rao et al. (1997) Oxidant-induced disruption of intestinal epithelial barrier function: role of protein tyrosine phosphorylation. American Journal of Physiology 273: G812–G823.

Riechel, T L., Sawyer, D T. (1975) Electrochemical studies of vanadium (III), -(IV), and -(V) Complexes of 8-quinolinol in acetonitrile. Formation of a binuclear mixed-valence (IV,V) complex. Inorg Chem. 14(8): 1869–1875.

Rodriguez et al. (1994) A simple spectrophotometric determination of submicromolar quantities of vanadium oxyions. Journal of Pharmaceutical & Biomedical Analysis. 12(12):1597–9.

Sabbioni et al. (1978) Similarity in metabolic patterns of difference chemical species of vanadium in the rat. Bioinorg. Chem. 8: 503–515.

Sabbioni et al. (1991) Cellular retention, cytotoxicity and morphological transformation by vanadium (IV) and vanadium (V) in BALB/3T3 cell lines. Carcinogenesis 12, 47–52.

Sakurai et al. (1980) Detection of oxovanadium (IV) and characterization of its ligand environment in subcellular fractions of the liver of rats treated with pentavalent vanadium (V). Biochem Biophys Res Comm 96(1): 293–298.

Sakurai et al. (1990) Insulin mimetic action of vanadyl complexes. J. Clin Biochem Nutr. 8: 193–200.

Sakurai H, (1994) Vanadium distribution in rats and DNA cleavage by vanadyl complex: implication for vanadium toxicity and biological effects., Environ Health Perspect Suppl 3: 35–6.

Tolman E L; Barris E; Burns M; Pansini A; and Partridge R (1979). Effects of vanadium on glucose metabolism in vitro. Life Sci. 25, 1159–1164.

Wiedmann et al. (1989). K-edge X-ray absorption spectra of biomimetic oxovanadium coordination compounds. Chemical Physics 136 (405–412).

Williams et al. (1996). A spectrophotometric study of the interaction of VO2+ with cytosine in nucleotides. Journal of Inorganic Biochemistry. 61(4):285–9.

Younes M, Strubelt O; (1991) Vanadate-induced toxicity towards isolated perfused rat livers: the role of lipid peroxidation.; Toxicology 66:1 63–74.

Patent References: EP 305246,N2S2; WO 9306811; WO 9702818

U.S. Patent Refs: U.S. Pat. No. 4,425,427 Luderer; U.S. Pat. No. 4,734,376 Pacey GE et al.; U.S. Pat. No. 4,882,171 Posner, B. et al.; U.S. Pat. No. 5,023,358 Lazaro R et al.; U.S. Pat. No. 5,069,913 Posner, B. et al.; U.S. Pat. No. 5,300,496 McNeill et al.; U.S. Pat. No. 5,338,759 Schechter Y et al.; U.S. Pat. No. 5,453,619 Asselain M et al U.S. Pat. No. 5,527,790 McNeill et al.; U.S. Pat. No. 5,545,661 Cullinan G J; U.S. Pat. No. 5,547,685 Cullinan G J; U.S. Pat. No. 5,601,080 Oppenheimer L.; U.S. Pat. No. 5,620,967 McNeill et al.; U.S. Pat. No. 5,688,784 McNeill et al.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

What is claimed is:

1. A colorimetric method for the determination of the presence of total vanadium, and of the concentrations of vanadyl and vanadate in a sample, the method comprising:

combining a sample suspected of comprising either or both of vanadyl and vanadate with a colorimetric substrate of the formula:

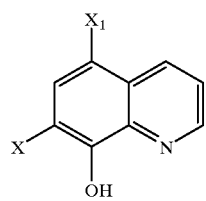

where X and $X_1$ are, independently, halogen substituents;

wherein the complex of said substrate provides a differential light absorption for vanadyl and vanadate, in the presence of a solvent that minimizes vanadyl oxidation;

reading the absorbance of said sample at a first wavelength that provides a measure of the combined vanadyl and vanadate concentration;

reading the absorbance of said sample at a second wavelength that provides a measure of the vanadate concentration;

wherein the concentration of total vanadium is proportional to the absorbance at said first wavelength, and the concentration of vanadate is proportional to the absorbance at said second wavelength.

2. The method of claim 1, wherein said colorimetric substrate is 5,7-dibromo-8-hydroxyquinoline.

3. The method of claim 2, wherein said first wavelength is 400 nm.

4. The method of claim 3, wherein said second wavelength is 525 nm.

5. The method of claim 4, wherein said buffer that minimizes vanadyl oxidation is acidic isopropanol.

6. The method of claim 1, wherein said sample is an environmental sample.

7. The method of claim 1, wherein said sample is a biological sample.

8. The method of claim 1, wherein said sample is a manufacturing sample.

9. The method of claim 1, wherein said sample comprises bis(ethylmaltolato)oxovanadium.

10. The method of claim 1, wherein said concentration of total vanadium and said concentration of vanadate is determined by comparison with a known standard.

11. The method of claim 1, further comprising repeating said determination of the presence of total vanadium, and of the concentrations of vanadyl and vanadate in a sample, over a time course.

12. A kit for colorimetric determination of the presence of total vanadium, and of the concentrations of vanadyl and vanadate in a sample, the kit comprising:

vanadyl standards;

vanadate standards;

colorimetric substrate of the formula:

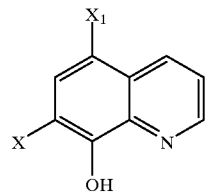

where
X and $X_1$ are, independently, halogen substituents;
and a solvent that minimizes vanadyl oxidation.

13. The kit according to claim 12, wherein said colorimetric substrate is 5,7-dibromo-8-hydroxyquinoline.

14. The kit according to claim 13, wherein said buffer that minimizes vanadyl oxidation is acidic isopropanol.

* * * * *